(12) United States Patent
Crider et al.

(10) Patent No.: US 9,131,682 B2
(45) Date of Patent: Sep. 15, 2015

(54) ANTIBACTERIAL COMPOSITION WITH LOW AMOUNTS OF SURFACTANT AND ANTIBACTERIAL ACTIVES

(71) Applicant: The Dial Corporation, Scottsdale, AZ (US)

(72) Inventors: Kanani Crider, Phoenix, AZ (US); Chris Luciow, Phoenix, AZ (US); Janice L. Fuls, Fountain Hills, AZ (US); Nancy D. Rodgers, Chandler, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 14/054,799

(22) Filed: Oct. 15, 2013

(65) Prior Publication Data

US 2015/0105473 A1 Apr. 16, 2015

(51) Int. Cl.
*A61K 31/66* (2006.01)
*A01N 25/30* (2006.01)
*A01N 25/00* (2006.01)

(52) U.S. Cl.
CPC ............. *A01N 25/30* (2013.01); *A01N 25/00* (2013.01)

(58) Field of Classification Search
USPC .......................................... 510/131, 138, 130
See application file for complete search history.

(56) References Cited

U.S. PATENT DOCUMENTS 6,518,229 B2 * 2/2003 Tashjian et al. ................ 510/131
7,601,731 B2 * 10/2009 Raad ............................. 514/279

* cited by examiner

*Primary Examiner* — Rei-Tsang Shiao
(74) *Attorney, Agent, or Firm* — David K. Benson

(57) ABSTRACT

An antibacterial composition includes at least one surfactant that is less than 6.0 weight percent of the composition and at least one antibacterial active that is less than 0.2 weight percent of the composition. The composition also has a pH between 6.0 and 6.5. The composition also exhibits an efficacy characteristic that results in a logarithmic reduction of at least 2.0 of a bacterial population based on measurements taken from of a user's hand.

12 Claims, No Drawings

US 9,131,682 B2

ANTIBACTERIAL COMPOSITION WITH LOW AMOUNTS OF SURFACTANT AND ANTIBACTERIAL ACTIVES

FIELD OF THE INVENTION

The present invention generally relates to antibacterial compositions, and more particularly relates to antibacterial compositions that are configured for hand soaps and body washes.

BACKGROUND OF THE INVENTION

Antibacterial compositions, such as hand soaps and body washes, are typically used to clean a user's skin and to destroy bacteria and other microorganisms on the skin. Often, these antibacterial compositions are used on the user's hands, arms, face, and other parts of the user's body. Often, the antibacterial products will include surfactants which act to both destroy bacteria and remove the bacteria from the skin.

Some commercial antibacterial products will include surfactants that make up 20.0 weight percent or more of the antibacterial compositions to achieve the antibacterial efficacious standards established by the Food and Drug Administration (FDA) of the United States. Unfortunately, high levels of surfactants can cause skin irritation.

Accordingly, it is desirable to have antibacterial compositions that meet FDA standards while having lower levels of surfactants. In addition, it is desirable that the antibacterial compositions be less prone to causing skin irritation. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An antibacterial composition includes at least one surfactant that is less than 6.0 weight percent of the composition and at least one antibacterial active that is less than 0.2 weight percent of the composition. The composition also has a pH between 6.0 and 6.5. The composition also exhibits an efficacy characteristic that results in a logarithmic reduction of at least 2.0 of a bacterial population based on measurements taken from of a user's hand.

An antibacterial product includes a gel that has a pH between 6.0 and 6.5. The gel further has an antibacterial component consisting of at least one surfactant that is less than 6.0 weight percent of the gel and at least one antibacterial active that is less than 0.2 weight percent of the gel. The gel also exhibits an efficacy characteristic that results in a logarithmic reduction of at least 2.0 of a bacterial population based on measurements taken from of a user's hand.

A composition includes an antibacterial component including sodium laureth sulfate and cocamidopropyl betaine where the sodium laureth sulfate is 4.5 to 5.0 weight percent of the composition and cocamidopropyl betaine is 0.8 to 1.2 weight percent of the composition. The antibacterial component also includes triclosan having 0.08 to 0.15 weight percent of the composition. Further, the composition has a pH between 6.0 and 6.5. The composition also exhibits an efficacy characteristic that results in a logarithmic reduction of at least 2.0 of a bacterial population based on measurements taken from of a user's hand.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Antibacterial activity is determined by measuring populations of microorganisms, including both Gram positive and Gram negative microorganisms. The log reduction or percent reduction in bacterial populations resulting from the antibacterial composition correlates to the reduction of bacterial activity. Generally, the reduction in bacterial populations is measured in beakers before and after an application of the antibacterial composition. The difference between the measurements is determined to be the log reduction or percent reduction in the bacterial population.

It should be noted that high population reductions have been achieved at pH values of 4.0 and 9.0, but such log reductions are attributed at least in part to these relatively extreme pH values. Compositions having extreme pH values can also irritate the skin, and are thus generally avoided. Traditionally, it has been difficult to achieve a high log reduction using an antibacterial composition having a neutral pH of about 5.0 to about 8.0, and especially about 6.0 to about 8.0.

Some commercial antibacterial compositions include an antibacterial active that contributes to killing bacteria. However, increased usage of the antibacterial actives does not typically have a proportional increase in antibacterial efficacy. Some believe that the surfactants interfere with the antibacterial actives by blocking the antibacterial actives from coming into contact with the bacteria. Accordingly, the blocked antibacterial actives' effect on the bacteria is slower than desired. Unfortunately, the slower process typically results in the antibacterial active being washed away before the antibacterial active can kill the bacteria. To complicate matters, some antibacterial actives do not dissolve well in water. For example, phenol based antibacterial actives, which includes triclosan, have poor solubility in water. To increase the solubility of the phenol based antibacterial actives, more surfactants are typically added to the antibacterial composition, which results in an increased probability that a user will experience skin irritation.

The principles described herein overcome these deficiencies by including a lower amount of both the antibacterial actives and the surfactants. Surprisingly, tests indicated that using a surfactant level that was 6.0 weight percent or less of the antibacterial composition as well as using an antibacterial active that was 0.2 weight percent or less of the antibacterial composition yielded results that met the FDA's efficacy standards. Further, the tests indicated that such antibacterial compositions were most effective in the pH range of 6.0 to 6.5. Such results are contrary to the understanding of the industry where it was believed that higher amounts of either the antibacterial active or the surfactant would yield an increase in the antibacterial log reduction. However, test results have confirmed that keeping the levels of the antibacterial active and the surfactants below what would have otherwise been considered acceptable levels yield satisfactory results in the neutral pH ranges which have been the most difficult pH range to meet the FDA's efficacy standards. These principles may be applied to any appropriate type of antibacterial composition. In some examples, the antibacterial composition is a liquid soap, a gel, a foaming soap, a hand soap, a body wash, another appropriate type of cleansing products, or combinations thereof.

As an example, one test included ingredients that make up an antibacterial component of the antibacterial composition as follows:

TABLE 1

| Ingredient | Weight Percent |
| --- | --- |
| Sodium Laureth Sulfate | 4.42 |
| Cocamidopropyl Betaine | 1.00 |
| Triclosan | 0.12 |

The sodium laureth sulfate and cocamidopropyl betaine are both surfactants. Thus, the combined surfactants made a 5.42 weight percent of the overall antibacterial composition. Furthermore, the triclosan is an antibacterial agent, and thus, the antibacterial active made up 0.12 weight percent of the overall antibacterial composition.

These ingredients may form an antibacterial component of the antibacterial composition. The antibacterial component is the portion of the antibacterial composition that contributes to killing bacteria and other microorganisms. The remainder of the antibacterial composition may include water and other ingredients that do not directly contribute to killing the bacteria and other microorganisms. Such other ingredients may include viscosity thickeners, fragrances, coloring agents, and pH adjusters that maintain a neutral pH level of the antibacterial composition, ingredients with other functions, or combinations thereof. In some examples, the antibacterial composition and/or antibacterial component contain no or very little alcohol that is configured to directly kill the bacteria as an ingredient in the antibacterial composition. Furthermore, in some examples, the antibacterial composition contains no or very little solvent. Some commercially available antibacterial compositions include solvents for purposes that do not involve killing bacteria.

In the example of Table 1, the antibacterial composition had a pH level of 6.15, and the antibacterial population was measured to have a 2.3 log 10 reduction, which meets the FDA's antibacterial efficacy standards. For this example, the log reduction measurements were taken off of the subject's skin. Briefly, subjects' hands were contaminated by pressing down onto sterile paper towels which had been inoculated with approximately $1.0 \times 10^4$ cfu/mL of bacteria. A baseline sampling was done by inserting the subjects' contaminated hands into bags and adding 75 mL of stripping solution. The hands were massaged for 1 minute and an aliquot of broth was removed and plated onto tryptic soy agar. Following baseline treatment, the subjects' hands were washed with a mild plain soap to remove any neutralizers left on the hands from the stripping solution. The subjects' hands were then contaminated again with *Serratia marscesens* using the same paper towel procedure. Following contamination subjects washed their hands with the test product and the hands were sampled as described above. The difference in bacterial populations determined the log reduction.

A surfactant is a compound that lowers the surface tension of a liquid or the interfacial tension between two liquids or between a liquid and a solid. Surfactants have a hydrophobic end and a hydrophilic end. The hydrophobic end has an uncharged carbohydrate group that can be straight, branched, cyclic, or aromatic. Depending on the nature of the hydrophilic part, the surfactants are classified as anionic, nonionic, cationic, or amphoteric. Anionic surfactants have a hydrophilic end that has a negatively charged group like a sulfonate, sulfate, or carboxylate and are sensitive to water hardness. Nonionic surfactants include a non-charged hydrophilic part, e.g. an ethoxylate. Cationic surfactants have a hydrophilic end that contains a positively-charged ion. Amphoteric surfactants or Zwitterionic surfactants have both cationic and anionic centers attached to the same molecule. The surfactants in the composition may include any appropriate type of surfactant or combinations of surfactants. For example, the surfactants may include a blend of multiple different types of surfactants.

Examples of surfactants which may be used to make the antibacterial composition include sodium laureth sulfate, cocamidopropyl betaine, polyoxyethylene sorbitan fatty acid esters, polyoxyethylene stearates, polyvinyl alcohol, poloxamers, octoxynols, sodium or ammonium salts of sarcosinates, sulfosuccinates, sulfonates, isethionates, sulfates, amine oxides, taurates, betaines, sultaines, imidazolines, ammonium cocoyl isethionate, their derivatives, and combinations thereof.

Specific anionic surfactants that may be used in the antibacterial composition include Cg-Clg alkyl sulfate, a Cg-Clg fatty acid salt, a Cg-Clg alkyl ether sulfate having one or two moles of ethoxylation, a Cg-Clg alkamine oxide, a Cg-Clg alkoyl sarcosinate, a Cg-Clg sulfoacetate, a Cg-Clg sulfosuccinate, a Cg-Clg alkyl diphenyl oxide disulfonate, a Cg-Clg alkyl carbonate, a Cg-Clg alpha-olefin sulfonate, a methyl ester sulfonate, and mixtures thereof. The Cg-Clg alkyl group can contain eight to sixteen carbon atoms, and can be a straight chain (e.g., lauryl) or branched (e.g., 2-ethylhexyl). The cation of the anionic surfactant can be an alkali metal (preferably sodium or potassium), ammonium, C1-C4 alkylammonium (mono-, di-, tri), or CC C3 alkanolammonium (mono-, di-, tri). Lithium and alkaline earth cations (e.g., magnesium) can be used. Other anionic surfactants that may be used in antibacterial composition include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear C10 diphenyl oxide disulfonates, lauryl sulfosuccinates, lauryl ether sulfates, myristyl sulfates, oleates, stearates, tallates, ricinoleates, cetyl sulfates, and combinations thereof.

Examples of nonionic surfactants which may be used to make the antibacterial composition include surfactants having a hydrophobic base, such as a long chain alkyl group or an alkylated aryl group, and a hydrophilic chain having a sufficient number (i.e., 1 to about 30) of ethoxy and/or propoxy moieties. Other examples of nonionic surfactants that may be used include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty (Cg-Clg) acids, condensation products of ethylene oxide with long chain amines or amides, mixtures thereof, or combinations thereof.

Additional examples of nonionic surfactants that may be used to make the antibacterial composition include, but are not limited to, methyl gluceth-lO, PEG-20 methyl glucose distearate, PEG-20 methyl glucose sesquistearate, C11-15 pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, ethoxylated nonylphenol, ethoxylated octylphenol, ethoxylated dodecylphenol, or ethoxylated fatty (C6-C22) alcohol, including 3 to 20 ethylene oxide moieties, polyoxyethylene-20 isohexadecyl ether, polyoxyethylene-23 glycerollaurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Examples of cationic surfactants may include amine oxides and amidoamine oxides, like cocamine oxide, decylamine oxide, and myristyl amine oxide, for example. Examples of ampholytic surfactants may include sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyldodecyl amino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

Any appropriate type of antibacterial active may be used according to the principles described herein. For example, the antibacterial active may include triclosan, bisguanidine, diphenyl compounds, benzyl alcohols, trihalocarbanilides, quaternary ammonium compounds, ethoxylated phenols, phenolic compounds, halo-substituted phenolic compounds, p-chloro-m-xylenol, includephenolic compounds, 2-hydroxydiphenyl compounds, chlorophenols (0-, m-, p-), 2,4-dichlorophenol, p-nitrophenol, picric acid, xylenol, p-chloro-m-xylenol, cresols (0-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, 4-phenolsulfonic acid, diphenyl compounds, hexachlorophene, tetrachlorophene, dichlorophen, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine.

Table 2 includes ingredients for an example of an antibacterial composition as follows:

TABLE 2

| Ingredient | Weight Percent |
|---|---|
| Water | Q.S. |
| Sodium Laureth Sulfate | 4.42 |
| Cocamidopropyl Betaine | 1.00 |
| Triclosan | 0.12 |
| PEG-18 Glyceryl Oleate/Cocoate | 0.75 |
| Mackam BC 39 | 3.50 |
| Polyquaternium 7 | 0.50 |
| DMDM Hydantoin | 0.22 |
| Tetrasodium EDTA | 0.04 |
| Citric Acid, Anhydrous | 0.04 |
| Sodium Chloride | 1.20 |

Similar to the example in Table 1, the sodium laureth sulfate, cocamidoproyl betaine, and triclosan make up the antibacterial component of the antibacterial composition. The other ingredients contribute to the overall characteristics of the antibacterial composition, but not directly to killing bacteria.

The PEG-18 glyceryl oleate/cocoate is an emulsifying agent that causes the surfactant to be evenly distributed throughout the antibacterial composition by preventing the surfactant from separating from the water in the composition. Any appropriate type of emulsifying agent may be used. The PEG-18 glyceryl oleate/cocoate is available for purchase under the trade name Antil® 171 from Evonik Industries AG, which has a location in Essen, Germany. The Mackam® BC 39 is another emulsifier. The Mackam® BC 39 is available for purchase through Solvay SA, located in Brussels, Belgium.

Polyquaternium 7 is a copolymer of acrylamide and diallyldimethylammonium chloride. Polyquaternium 7 may be used to neutralize the electrochemical charges in the antibacterial composition. Polyquaternium 7 is available under trade name Merquat™ S through Lubrizol, which is located in Wickliffe, Ohio, United States of America.

The DMDM Hydantoin is a preservative. DMDM Hydantoin is available for purchase under Glydant™ through Lonza, which headquartered in Basal, Switzerland. Tetrasodium EDTA (ethylenediaminetetraacetic acid) is a sequestering agent that is used to improve the antibacterial composition's stability in air.

The citric acid in the anhydrous form can be used as a pH adjuster. Often, surfactants are alkaline, causing the overall composition to have a higher pH. The pH adjusters may have a lower pH to bring the pH level for the overall composition into the 6.0 to 6.5 range. In other examples, the compositions pH may be lower, and the pH adjusters are used to increase the pH to the 6.0 to 6.5 range. Examples of pH adjusters that may be used in the antibacterial composition include basic pH adjusters, such as ammonia; mono-, di-, and tri-alkyl amines; mono-, di-, and tri-alkanolamines; alkali metal and alkaline earth metal hydroxides; sodium, potassium, and lithium hydroxide; monoethanolamine; triethylamine; isopropanolamine; diethanolamine; triethanolamine, mixtures thereof, or combinations thereof. Examples of acidic pH adjusters are the mineral acids and polycarboxylic acids. Non-limiting examples of mineral acids include hydrochloric acid, nitric acid, phosphoric acid, and sulfuric acid. Nonlimiting examples of polycarboxylic acids are citric acid, glycolic acid, lactic acid, mixtures thereof, or combinations thereof.

A viscosity thickener is a compound capable of increasing the viscosity of a water-based composition, or capable of converting a water based composition to a gel or semisolid so that the antibacterial composition can be easily applied to and rubbed onto skin. The antibacterial composition may include viscosity thickeners in sufficient amounts to make the antibacterial composition a gel or a viscous liquid soap. Examples of viscosity thickeners that may be used in the antibacterial composition may include, but are not limited to, hydroxypropyl methylcellulose, hydroxypropyl cellulose, hydroxyethyl cellulose, carbomer, polyquaterniums, carboxymethylcellulosics, naturally occurring gums, such as guar, guar derivatives, other cellulosic gums, polyacrylates, alginate, and alginate derivatives, natural or synthetic polymers or derivatives of natural polymers, and mixtures of these. For some compositions, the viscosity thickeners may make up to 5.0 weight percent of the antibacterial composition. In some examples, the viscosity thickeners may make up 0.5 to 2.0 weight percent of the antibacterial composition.

Any appropriate method of making the antibacterial compositions may be used. In examples where a viscosity thickener, such as cocamide mea, is used, the method may include adding water to the sodium laureth sulfate and then heating the combination to approximately 145 degrees F. or another appropriate temperature to melt the viscosity thickener. At this temperature, the cocamidopropyl betaine is added, and the remaining water is added. The solution is allowed to cool down to 100 degrees F. or less. Next, a premix of triclosan, any fragrances, the PEG-18 glyceryl oleate/cocoate, and the Mackam® BC 39 is added. Then, the remaining ingredients are added in the successive order that the remaining ingredients are listed in Table 2. The pH and viscosity can be adjusted as desired with appropriate thickeners and adjusters.

While the examples above have been described with reference to specific surfactant weight percents, any appropriate weight percent may be used. For example, the surfactant weight percent of the antibacterial composition may be less than 6.0 weight percent, less than 5.0 weight percent, less than 4.0 weight percent, less than 3.0 weight percent, between 4.0 and 5.7 weight percent, another weight percent, or combinations thereof.

Further, while the examples above have been described with reference to specific antibacterial weight percents, any appropriate weight percent may be used in accordance with the principles described herein. For example, the antibacterial active may have less than 0.20 weight percent, less than 0.15 weight percent, less than 0.10 weight percent, less than 0.05 weight percent, between 0.08 and 0.018 weight percent, another weight percent, or combinations thereof.

Additionally, while the examples above have been described with specific reference to properties exhibited by the antibacterial composition, any appropriate property may be exhibited. For example, the composition may exhibit an efficacy that results in a logarithmic reduction of at least 2.0 of a bacterial population based on measurements taken off of a user's hand. In other examples, the composition may exhibit an efficacy that results in a logarithmic reduction between 2.0 and 2.5 or greater than 2.5.

Also, while the examples above have been described with specific reference to pH levels of the antibacterial composition, any appropriate pH range according to the principles described herein may be used. For example, the pH level may between 6.0 and 6.5, between 6.1 and 6.4, within another appropriate range, or combinations thereof.

In some examples, the antibacterial composition is held within a container that has a pump that allows the antibacterial composition to be moved out of the container onto a user's hand. In some examples, the pump has a foaming mechanism. In other examples, the composition is a gel, and the pump does not cause the antibacterial composition to foam as the composition is moved out of the container. While the container has been described with reference to specific features, any appropriate type of container may be used to hold and apply the antibacterial composition to the user's skin.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An antibacterial composition, comprising:
   at least one anionic surfactant at a concentration that is less than 4.5 weight percent of the composition; and
   triclosan, at a concentration that is less than 0.2 weight percent of the composition;
   wherein the composition has a pH between 6.0 and 6.5 and the composition exhibits an efficacy characteristic that results in a logarithmic reduction of at least 2.0 of a bacterial population based on measurements taken from of a user's hand.

2. The composition of claim 1, wherein the antibacterial active constitutes between 0.08 and 0.18 weight percent of the composition.

3. The composition of claim 1, wherein the composition is a viscous liquid soap.

4. The composition of claim 1, wherein the logarithmic reduction of the bacterial population is between 2.0 to 2.5.

5. The composition of claim 1, wherein the composition comprises a pH adjustor selected from a group consisting of acids, mineral acids, polycarboxylic acids, hydrochloric acid, nitric acid, phosphoric acid, sulfuric acid, citric acid, glycolic acid, and lactic acid.

6. An antibacterial product, comprising:
   a gel having a pH between 6.0 and 6.5;
   at least one anionic surfactant at a concentration that is less than 4.5 weight percent of the gel; and
   triclosan at a concentration that is less than 0.2 weight percent of the gel;
   wherein the gel exhibits an efficacy characteristic that results in a logarithmic reduction of at least 2.0 of a bacterial population based on measurements taken from of a user's hand.

7. The product of claim 6, wherein the antibacterial active constitutes between 0.08 and 0.18 weight percent of the gel.

8. A composition, comprising:
   sodium laureth sulfate and cocamidopropyl betaine where the sodium laureth sulfate comprises less than 4.5 weight percent of the composition and cocamidopropyl betaine comprises 0.8 to 1.2 weight percent of the composition; and
   triclosan at a concentration of 0.08 to 0.15 weight percent of the composition;
   wherein the composition has a pH between 6.0 and 6.5 and the composition exhibits an efficacy characteristic that results in a logarithmic reduction of at least 2.0 of a bacterial population based on measurements taken from of a user's hand.

9. The composition of claim 8, wherein the composition comprises a pH adjustor selected from a group consisting of acids, mineral acids, polycarboxylic acids, hydrochloric acid, nitric acid, phosphoric acid, sulfuric acid, citric acid, glycolic acid, and lactic acid.

10. The composition of claim 8, wherein the logarithmic reduction of the bacterial population is between 2.0 to 2.5.

11. The composition of claim 8, wherein the composition comprises viscosity thickeners.

12. The composition of claim 8, wherein the pH is between 6.1 and 6.4.

* * * * *